US012797106B2

(12) United States Patent
Nie et al.

(10) Patent No.: US 12,797,106 B2
(45) Date of Patent: Nov. 17, 2026

(54) ULTRASONIC SURGICAL INSTRUMENT AND PROCESSING AND ASSEMBLING METHOD

(71) Applicant: EZISURG MEDICAL CO., LTD., Shanghai (CN)

(72) Inventors: Honglin Nie, Shanghai (CN); Menghui Liao, Shanghai (CN); Guang Yang, Shanghai (CN); Yongchun Zhang, Shanghai (CN); Chuangang Tang, Shanghai (CN)

(73) Assignee: EZISURG MEDICAL CO., LTD., Shanghai (CN)

( * ) Notice: Subject to any disclaimer, the term of this patent is extended or adjusted under 35 U.S.C. 154(b) by 176 days.

(21) Appl. No.: 18/555,700

(22) PCT Filed: Apr. 15, 2022

(86) PCT No.: PCT/CN2022/087173
§ 371 (c)(1),
(2) Date: Oct. 16, 2023

(87) PCT Pub. No.: WO2022/218422
PCT Pub. Date: Oct. 20, 2022

(65) Prior Publication Data

US 2024/0197355 A1 Jun. 20, 2024

(30) Foreign Application Priority Data

Apr. 16, 2021 (CN) ........................ 202110409157.X

(51) Int. Cl.
*A61B 17/32* (2006.01)
*A61B 17/00* (2006.01)

(52) U.S. Cl.
CPC ................. *A61B 17/320092* (2013.01); *A61B 2017/00367* (2013.01); *A61B 2017/00526* (2013.01); *A61B 2017/320094* (2017.08)

(58) Field of Classification Search
CPC .... A61B 17/320092; A61B 17/320068; A61B 2017/320094; A61B 2017/320093
See application file for complete search history.

(56) References Cited

U.S. PATENT DOCUMENTS 11,759,228 B2 9/2023 Nie et al.
2006/0241532 A1 10/2006 Murakami
(Continued)

FOREIGN PATENT DOCUMENTS

CN 202908803 U 5/2013
CN 104783866 A 7/2015
(Continued)

OTHER PUBLICATIONS

English translation for WO-2019128876-A1, Nie, Honglin, Jul. 4, 2019.*
(Continued)

*Primary Examiner* — Sarah A Long
(74) *Attorney, Agent, or Firm* — ARENTFOX SCHIFF LLP

(57) ABSTRACT

An ultrasonic surgical instrument has an easily assembled cannula assembly. The instrument includes an ultrasonic cutter bar for transmitting ultrasonic mechanical energy, wherein the cannula assembly is coaxially mounted around the ultrasonic cutter bar, and the cannula assembly is provided with the jaw at a distal end thereof and a handle assembly at a proximal end thereof. The cannula assembly has an integral structure and is connected to the handle assembly by means of a connecting mechanism. The integral cannula assembly can reduce assembly procedures, simplify
(Continued)

A a mounting structure, reduce complex structures, generally reduce the cost of manufacturing instruments, and reduce the wound on patients.

8 Claims, 5 Drawing Sheets

(56) References Cited

U.S. PATENT DOCUMENTS

| | | | | |
|---|---|---|---|---|
| 2009/0036913 | A1* | 2/2009 | Wiener | A61B 17/320092 606/169 |
| 2017/0319229 | A1 | 11/2017 | Brown et al. | |
| 2019/0262028 | A1 | 8/2019 | Netzel | |
| 2020/0345880 | A1 | 11/2020 | Leuck et al. | |
| 2021/0030436 | A1* | 2/2021 | Swearingen | A61B 17/320092 |
| 2022/0287736 | A1 | 9/2022 | Liu et al. | |

FOREIGN PATENT DOCUMENTS

| | | | | |
|---|---|---|---|---|
| CN | 108354652 | A | 8/2018 | |
| CN | 108969058 | A | 12/2018 | |
| CN | 109009330 | A | 12/2018 | |
| CN | 211187447 | U | 8/2020 | |
| CN | 211609975 | U | 10/2020 | |
| CN | 113057715 | A | 7/2021 | |
| JP | 2003-502102 | A | 1/2003 | |
| JP | 2009-261912 | A | 11/2009 | |
| JP | 2010-167084 | A | 8/2010 | |
| WO | 2001/024713 | A1 | 4/2001 | |
| WO | 2017/100412 | A1 | 6/2017 | |
| WO | WO-2019128876 | A1 * | 7/2019 | A61B 17/320092 |

OTHER PUBLICATIONS

International Search Report issued in corresponding International Application PCT/CN2022/087173, mailed Jun. 29, 2022, and an English Translation thereof.

Written Opinion issued in corresponding International Application PCT/CN2022/087173, mailed Jun. 29, 2022, and English Translation thereof.

Extended European Search Report and Search Opinion received for European Application No. 22787644.8, mailed on Feb. 26, 2025, 10 pages.

Office Action received for Japanese Patent Application No. 2023-562837, mailed on Apr. 28, 2025, 16 pages (8 pages of English Translation and 8 pages of Original Document).

Office Action received for Japanese Patent Application No. 2023-562837, mailed on Jan. 9, 2025, 38 pages (19 pages of English Translation and 19 pages of Original Document).

Office Action received for Japanese Patent Application No. 2023-562837, mailed on Jul. 23, 2024, 21 pages (11 pages of English Translation and 10 pages of Original Document).

* cited by examiner

A

ULTRASONIC SURGICAL INSTRUMENT AND PROCESSING AND ASSEMBLING METHOD

CROSS-REFERENCE TO RELATED APPLICATIONS

This application is a national phase of International Application No. PCT/CN2022/087173, filed on Apr. 15, 2022, which claims priority to Chinese Patent Application No. 202110409157.X, filed on Apr. 16, 2021. The disclosures of the above applications are incorporated herein by reference in their entirety.

FIELD

The present disclosure relates to the field of surgical medical instruments, is applied to surgical instruments, and in particular relates to an ultrasonic surgical instrument and a processing and assembling method.

BACKGROUND

The statements in this section merely provide background information related to the present disclosure and may not constitute prior art.

With the popularization of minimally invasive surgery, ultrasonic scalpels have become a conventional surgical instrument. A cutter bar of the ultrasonic scalpel exhibits a mechanical oscillation at a specific ultrasonic frequency by means of an ultrasonic frequency generator, resulting in a vaporization of water molecules in tissues, a breakage of protein hydrogen bonds, and a disintegration of cells, thereby cutting or coagulating the tissues, and also closing blood vessels. The ultrasonic scalpel simultaneously performs tissue cutting and coagulation, and incurs relatively small lateral thermal damage. Clinical use of such instrument can achieve focal resection at lower temperature and with less bleeding, while minimizing tissue lateral thermal damage, so that the ultrasonic scalpel is more and more popular.

The ultrasonic scalpel is mainly composed of an ultrasonic frequency generator, a transducer, and a surgical instrument. The ultrasonic frequency generator transmits an oscillating electrical signal. The transducer initiates a mechanical vibration in response to the oscillating electrical signal. The surgical instrument cuts and coagulates tissues with the mechanical vibrations of the transducer. The surgical instrument is usually composed of a cutter bar, a jaw that form a clamping structure with the cutter bar, a cannula assembly that surrounds the cutter bar, and a handle assembly. The cutter bar transmits the mechanical vibrations of the transducer to the cutter bar. The cutter bar and the jaw cooperate with each other to clamp tissue for subsequent cutting and coagulating. The cannula assembly is composed of an outer cannula and an inner cannula. The cutter bar is located in the inner cannula. On the one hand, the cannula assembly isolates the cutter bar from the ambience so as to protect and support the cutter bar; and on the other hand, the cannula assembly forms a connecting rod mechanism with the jaw to drive the jaw to be closed and opened. The handle assembly is held in a doctor's hand and can control the jaw to be opened and closed. There is also a switch that can control the ultrasonic frequency generator to start or stop outputting the oscillating electrical signals.

The cutter bar assembly designed in the existing ultrasonic scalpel has a relatively complex structure, high manufacturing cost, and inconvenient assembling. The inner/outer cannula is assembled by processes such as an expandable tube and a spiral groove, resulting in high cost. Moreover, the inner/outer cannula is complex in structure and expensive, and has low processing efficiency.

As shown in FIG. 9, the inner cannula and the outer cannula of the existing ultrasonic scalpel are usually sealed by making an expanded groove structure. The ultrasonic scalpel shown in FIG. 9 includes an outer cannula assembly 21', an inner cannula assembly 22', a thumb wheel outer ring 23', and a sealing ring 24'. The thumb wheel outer ring 23', the outer cannula assembly 21', and the inner cannula assembly 22' form a gradually distributed structure from outside to inside. The sealing ring 24' is located between an outer cannula body 211' of the outer cannula assembly 21' and an inner cannula body 221' of the inner cannula assembly 22'. The outer cannula body 211' of the outer cannula assembly 21' and the inner cannula body 221' of the inner cannula assembly 22' each has a complex embossing structure. The inner cannula and the outer cannula are sealed by such complex embossing structure. That is, the cannula needs to be formed into a special configuration to achieve the sealing by being made into the expanded groove structure. Therefore, the cannula has a complicated structure, a complex processing process, and high cost.

Therefore, there is a need in this field for an ultrasonic surgical instrument (ultrasonic scalpel) that can eliminate or at least alleviate all or part of the drawbacks in the above-mentioned prior art.

SUMMARY

This section provides a general summary of the disclosure and is not a comprehensive disclosure of its full scope or all of its features.

In order to solve at least one of the drawbacks in the above-mentioned prior art, an ultrasonic surgical instrument that is reusable and easily assembled. The entire structure of the instrument is significantly simplified, and the cost of a cannula assembly is significantly reduced.

Meanwhile, the present disclosure can reduce assembling procedures by an integrated molding process. Components formed by the integral molding process (coinjection) are high in integrality. Furthermore, sealing between an inner cannula and an outer cannula does not need to be achieved by designing complex configurations (such as an expanded groove structure) of cannulas for cooperation, so that the expanded groove structures of the cannula parts can be eliminated or simplified, which greatly improves the overall performance of the ultrasonic surgical instrument. Thus, the ultrasonic surgical instrument can be applied to operation scenes with higher fineness.

According to one aspect of the present disclosure, an ultrasonic surgical instrument is provided, including: a cutter bar, a jaw, a cannula assembly, and a handle assembly, wherein the jaw and a distal end of the cutter bar form a clamping structure; the cutter bar is an ultrasonic cutter bar configured for transmitting ultrasonic energy; the cannula assembly and the cutter bar are coaxially arranged; the jaw is arranged at a distal end part of the cannula assembly; the handle assembly is arranged at a proximal end part of the cannula assembly; the cannula assembly includes an outer cannula assembly, an inner cannula assembly, and a thumb wheel outer ring; the outer cannula assembly and the inner cannula assembly are both monolithic structures (monolithic structures) and connected to the handle assembly through a connecting mechanism; the ultrasonic surgical instrument further includes a thumb wheel outer ring; the thumb wheel outer ring is coaxially mounted around the outer cannula assembly; and the thumb wheel outer ring and the outer cannula assembly cannot rotate relative to each other. The cannula assembly is rotatably connected to the handle assembly. The rotatable connection between the outer cannula assembly and the handle assembly is unremovable and restrains axial movement. A connecting structure, rotating coaxially with the handle assembly, on the cannula assembly is arranged on the outer cannula assembly or the thumb wheel outer ring. The outer cannula assembly is axially provided with an anti-rotation boss, the thumb wheel outer ring is provided with an anti-rotation groove, and the anti-rotation boss cooperates with the anti-rotation groove; or alternatively, the outer cannula assembly is axially provided with an anti-rotation groove, the thumb wheel outer ring is provided with an anti-rotation boss, and the anti-rotation boss cooperates with the anti-rotation groove. The outer cannula assembly is axially provided with a first anti-off boss, the thumb wheel outer ring is provided with a second anti-off boss, and the first anti-off boss of the outer cannula assembly cooperates with the second anti-off boss of the thumb wheel outer ring to assemble the outer cannula assembly with the thumb wheel outer ring. The thumb wheel outer ring and the outer cannula assembly are assembled by, but not limited to, interference fit or gluing, so that the thumb wheel outer ring and the outer cannula assembly cannot rotate relative to each other.

The ultrasonic surgical instrument of the present disclosure adopts the integral type cannula assembly. An expanded structure is not arranged (eliminated) in the cannula assembly, so that the ultrasonic surgical instrument is simple in structure and easy to assemble, and has reduced cost.

According to another aspect of the present disclosure, a processing and assembling method of an ultrasonic surgical instrument is provided. The ultrasonic surgical instrument includes a cutter bar, a jaw, a cannula assembly, and a handle assembly. The jaw and a distal end of the cutter bar form a clamping structure. The cannula assembly includes an outer cannula assembly and an inner cannula assembly. The processing and assembling method includes: assembling an outer cannula body and an outer cannula matrix into the outer cannula assembly by a coinjection molding process, a welding process, or a gluing process; assembling an inner cannula body and an inner cannula matrix into the inner cannula assembly by a coinjection molding process, a welding process, or a gluing process; coaxially mounting the outer cannula assembly and the inner cannula assembly to obtain the cannula assembly; and assembling the cannula assembly, the cutter bar, the jaw, and the handle assembly to obtain the ultrasonic surgical instrument.

The processing and assembling method of the ultrasonic surgical instrument according to the embodiments of the present disclosure may have the following beneficial effects:

Both the outer cannula assembly and the inner cannula assembly are monolithic structures, and the sealing between the inner and outer cannulas does not need to be achieved by designing complex configurations of cannulas. Expanded structures of the cannula parts can be eliminated or simplified. The overall structure is greatly simplified, and the performance is better optimized.

Further areas of applicability will become apparent from the description provided herein. It should be understood that the description and specific examples are intended for purposes of illustration only and are not intended to limit the scope of the present disclosure.

DRAWINGS

Drawings depicted herein are used for providing further understandings of the embodiments of the present disclosure, and constitute part of the present disclosure. Illustrative embodiments and descriptions thereof of the present disclosure are used for explaining the present disclosure, and do not constitute an improper limitation to the present disclosure. In the drawings.

Figure 1:
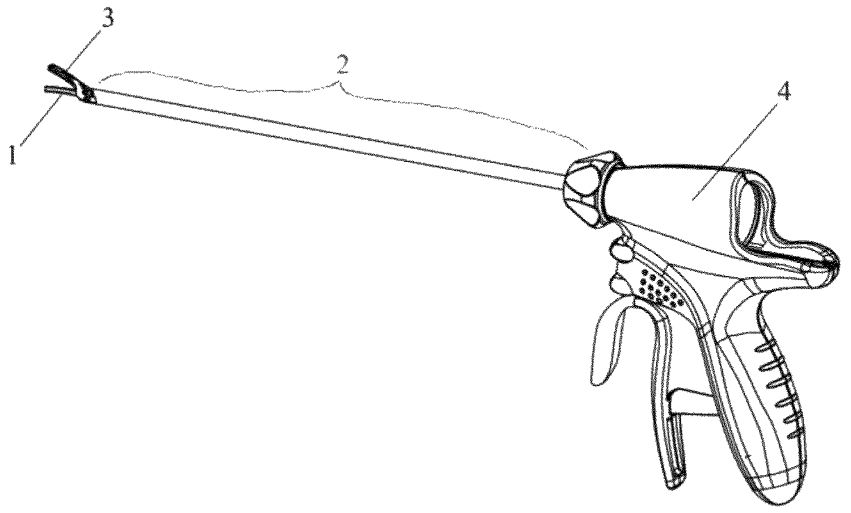
FIG. 1 is an overall schematic diagram of an ultrasonic surgical instrument of the present disclosure.

Reference numerals: 1: cutter bar; 2: cannula assembly; 3: jaw; 4: handle assembly; 21: outer cannula assembly; 22: inner cannula assembly; 23: thumb wheel outer ring; 24: sealing ring; 25: first mounting direction; 26: second mounting direction; 211: outer cannula body; 212: outer cannula matrix; 213: first anti-off boss; 214: anti-rotation boss; 215: connecting structure; 221: inner cannula body; 222: inner cannula matrix; 231: second anti-off boss; 232: anti-rotation groove; 21': outer cannula assembly; 22': inner cannula assembly; 23': thumb wheel outer ring; 24': sealing ring; 211': outer cannula body; and 212': outer cannula matrix.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

For the purpose of making objectives, technical solutions, and advantages of the present disclosure clearer, clear and complete descriptions will be made below to the technical solutions of the present disclosure in conjunction with specific embodiments and corresponding drawings of the present disclosure. Obviously, the described embodiments are a part of the embodiments of the present disclosure, not all the embodiments. Based on the embodiments in the present disclosure, all other embodiments obtained by those of ordinary skill in the art without creative work shall fall within the protection scope of the present disclosure.

In the prior art, Chinese patent application No. CN201220588716.4 (publication patent number CN202908803U) discloses a disposable ultrasonic scalpel, including a cutter head and a cutter bar. The cutter head includes a cutter head inner tube, a cutter head outer tube, and a cutter head body. The cutter bar includes a cutter bar inner tube, a cutter bar outer tube, and a cutter bar body. The cutter head inner tube, the cutter head outer tube, the cutter head body, the cutter bar inner tube, the cutter bar outer tube, and the cutter bar body are detachably connected together, respectively. The cutter head of the ultrasonic scalpel of the present disclosure can only be used once and is thus disposable, and so it has high usage costs.

Chinese patent application number CN201921215696.4 (publication patent number CN211187447U) discloses a shear-shaped, monolithic ultrasonic scalpel and surgical instrument. The shear-shaped, monolithic ultrasonic scalpel includes an ultrasonic actuating arm and a shear-shaped handle. The ultrasonic actuating arm includes a cutter bar and an ultrasonic transducer. The shear-shaped handle includes a first handle and a second handle. The ultrasonic actuating arm is non-detachably arranged on the first handle, and the ultrasonic actuating arm includes a limiting structure. The limiting structure is located in the first handle to limit the movement of the ultrasonic actuating arm. The ultrasonic scalpel of the present disclosure is also integrally made as a disposable sterile instrument and not reusable.

Chinese patent application No. CN201810130712.3 discloses a reusable ultrasonic scalpel. The ultrasonic scalpel includes a knife, a cutter bar assembly, and a functional assembly. The knife, the cutter bar assembly, and the functional assembly are connected in turn. The cutter bar assembly includes a cutter bar, and an inner cannula and an outer cannula which successively sleeve the cutter bar from inside to outside. The inner cannula is divided into an inner cannula at a jaw head end and an inner cannula at a rotating handle end, and the outer cannula is divided into an outer cannula at the jaw head end and an outer cannula at the rotating handle end. The inner cannula of the jaw head end and the inner cannula of the rotating handle end are clamped using an L-shaped clamping structure, and the outer cannula at the jaw head end and the outer cannula of the rotating handle end are clamped with an L-shaped clamping structure.

Chinese patent application No. CN201810871843.7 (publication patent number CN109009330A) discloses an ultrasonic scalpel, including a shell, a cutter bar assembly and a cannula unit which pass through the shell, and a trigger assembly movably connected to the cannula unit. The cutter bar assembly includes a core cutter bar unit and a handle unit, and the cannula unit includes an outer cannula, an inner cannula, two opposite inner cannula shells, an outer cannula shell, a rotating operating member, and a fixing device. An axial limiting device is arranged between the inner cannula shell and the inner cannula, and the fixing device is arranged between the outer cannula and the rotating operating member. A pin shaft unit is located in a first strip-shaped slot of the outer cannula and a third strip-shaped slot of the inner cannula.

Chinese patent application No. CN201811114966.2 (publication patent number CN108969058A) discloses a reusable ultrasonic scalpel, including a shell, a handle, a cutter bar assembly, a universal wheel, and a moving mechanism. The cutter bar assembly passes through the shell, and the handle is partially located in the shell and is connected to the cutter bar assembly. The universal wheel sleeves the cutter bar assembly, and the cutter bar assembly includes a core cutter bar, an inner cannula, and an outer cannula. The core cutter bar passes through the inner cannula. The outer cannula sleeves the inner cannula, and the core cutter bar is fixed with the handle axially and is connected to the outer cannula radially through a shaft pin in a limited manner. The moving mechanism is located in the shell and is connected to the inner cannula. One end of the universal wheel facing outer cannula is provided with a gap in which a silicone plug is arranged. A connecting part is provided with a cleaning notch, and the silicone plug is configured for closing the cleaning notch.

Chinese patent application No. CN201910752035.3 (publication patent number CN110448357A) discloses a reusable ultrasonic scalpel, including a handle assembly and an ultrasonic cutter bar which is arranged at a distal end of the reusable ultrasonic scalpel in an extending manner and configured for transmitting ultrasonic mechanical energy. The ultrasonic cutter bar is sleeved with a cannula assembly. The cannula assembly is detachably connected to the handle assembly through a quick connect mechanism.

The cutter bar assembly designed in the existing ultrasonic scalpel has a relatively complex structure, high manufacturing cost, and inconvenient assembling. The inner/outer cannula is assembled by processes such as an expandable tube and a spiral groove, resulting in high cost. Moreover, the inner/outer cannula is complex in structure and expensive, and has low processing efficiency.

The technical solutions provided by the embodiments of the present disclosure are described in detail below in conjunction with the accompanying drawings.

It is emphasized that unless otherwise specified, the terms used herein are consistent with the common meanings of various technical terms in the field, as well as the meanings of professional terms defined in various technical dictionaries, textbooks, and the like.

During orientation expression herein, the reference is generally assigned to an instrument operator. A position closer to the instrument operator is referred to as "proximal end", and a position farther to the instrument operator is referred to as "distal end". Further, a lengthwise direction of the ultrasonic scalpel can be referred to as an axial direction herein.

Referring to FIG. 1, an ultrasonic surgical instrument according to an embodiment of the present disclosure is shown. The surgical instrument usually includes a cutter bar 1, a jaw 3, a cannula assembly 2, and a handle assembly 4. The jaw 3 and a distal end of the cutter bar 1 form a clamping structure. The cannula assembly 2 surrounds the cutter bar 1.

The cutter bar 1 is an ultrasonic cutter bar configured for transmitting ultrasonic energy. The cannula assembly 2 and the cutter bar 1 are coaxially arranged. The jaw 3 is arranged at a distal end part of the cannula assembly 2. The handle assembly 4 is arranged at a proximal end part of the cannula assembly 2. The cannula assembly 2 is monolithic structure connected to the handle assembly 4 through a connecting mechanism.

During an operation, the handle assembly 4 is held in a doctor's hand, and the jaw 3 can be operated to be opened and closed. There is also a switch that can control an ultrasonic frequency generator to start or stop outputting oscillating electrical signals. The oscillating electrical signals activate mechanical vibrations by means of a transducer, and the cutter bar 1 transmits the mechanical vibrations of the transducer to the cutter bar. The cutter bar and the jaw 3 cooperate to clamp a tissue for subsequent ultrasonic cutting and hemostasis on the clamped tissue.

On the one hand, the cannula assembly 2 isolates the cutter bar 1 from the ambience to protect the cutter bar, and on the other hand, a distal end of the cannula assembly 2 forms a connecting rod mechanism with the jaw 3 to drive the jaw 3 to be closed and opened.

Figure 2:
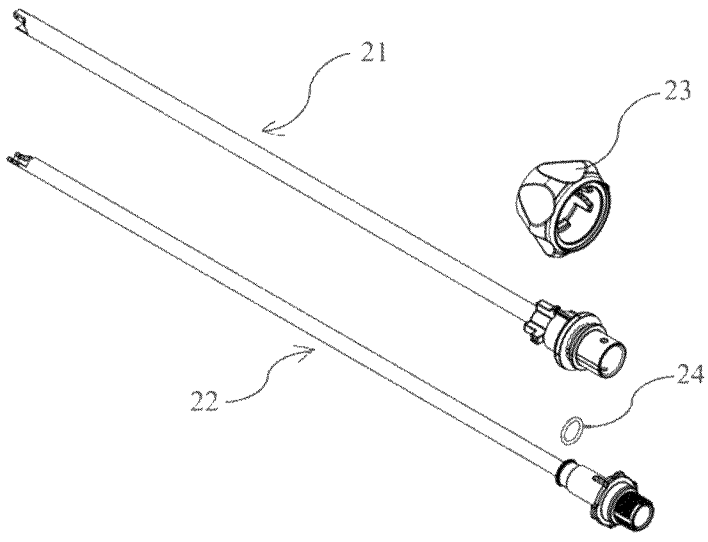
FIG. 2 is an exploded diagram of a cannula assembly of the present disclosure.

As shown in FIG. 2, an exploded diagram of the cannula assembly 2 of the ultrasonic surgical instrument of the present disclosure is shown. The cannula assembly 2 includes an outer cannula assembly 21, an inner cannula assembly 22, and a thumb wheel outer ring 23.

The outer cannula assembly 21 is coaxial with the inner cannula assembly 22 and the cutter bar 1, and the inner cannula assembly 22 is located between the outer cannula assembly 21 and the cutter bar 1, thus forming a structural sequence from outside to inside: namely, the outer cannula assembly 21—the inner cannula assembly 22—and the cutter bar 1.

Figure 3:
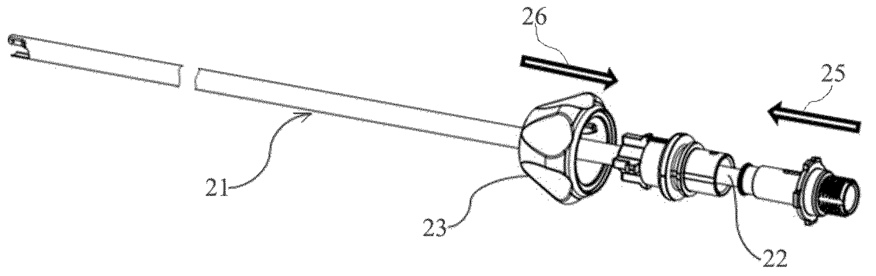
FIG. 3 is a schematic diagram of mounting of a cannula assembly of the present disclosure.

FIG. 3 further illustrates a schematic diagram of mounting of the cannula assembly 2 of the ultrasonic surgical instrument of the present disclosure. The ultrasonic surgical instrument further includes the thumb wheel outer ring 23. The inner cannula assembly 22 and the outer cannula assembly 21 are mounted coaxially, that is, along a first mounting direction 25 depicted in the figure. The inner cannula assembly 22 is plugged into a proximal end of the outer cannula assembly 21 from a distal end. Afterwards, the thumb wheel outer ring 23 is also mounted coaxially with the outer cannula assembly 21, that is, along a second mounting direction 26 depicted in the figure. Specifically, the thumb wheel outer ring 23 sleeves the outer cannula assembly 21 from the distal end.

The thumb wheel outer ring 23 cannot rotate relative to the outer cannula assembly 21.

Advantageously, the rotatable connection between the outer cannula assembly 2 and the handle assembly 4 is unremovable and restrains an axial movement.

The outer cannula assembly 21 is assembled together by an outer cannula body 211 and an outer cannula matrix 212 by a coinjection molding process, a welding process, or a gluing process. The inner cannula assembly 22 is assembled together by an inner cannula body 221 and the inner cannula matrix 222 by a coinjection molding process, a welding process, or a gluing process.

The assembled cannula assembly 2 is mounted on the handle assembly 4, and a drive assembly in the handle assembly 4 actuates the inner cannula assembly 22 of the cannula assembly 2. Relative movement between the inner cannula assembly 22 and the outer cannula assembly 21 achieves opening or closing of the jaw 3 and the cutter bar 1.

Circumferential rotation of the thumb wheel outer ring 23 drives the cannula assembly 2, the cutter bar 1, and the jaw 3 to rotate, making it convenient for doctors to adjust appropriate cutting and coagulation angles.

Figure 5:
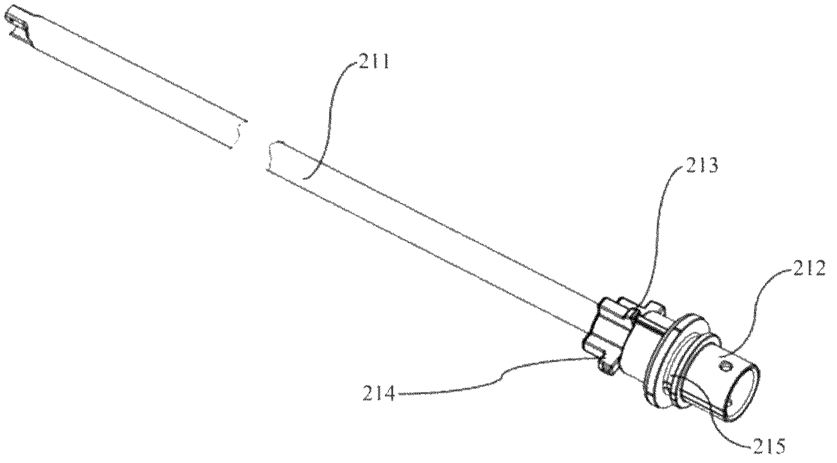
FIG. 5 is a schematic diagram of an outer cannula assembly of the present disclosure.

In an embodiment, as shown in FIG. 5, the outer cannula assembly 21 is composed of the outer cannula body 211 and the outer cannula matrix 212. The outer cannula body 211 and the outer cannula matrix 212 are arranged to be a monolithic structure.

An optional process is to integrate the outer cannula body 211 and the outer cannula matrix 212 by a coinjection molding technology. The monolithic structure formed by the coinjection molding technology has no connection gap, and has high integrity and convenient use.

A further optional process is to integrate the outer cannula body 211 and the outer cannula matrix 212 by welding or gluing. The outer cannula assembly 21 formed by these connection methods also has the advantages of high integrity and convenient use.

To facilitate the assembling with the thumb wheel outer ring 23, the outer cannula assembly 21 is provided with a first anti-off boss 213 and an anti-rotation boss 214. A quantity of the first anti-off boss 213 and a quantity of the anti-rotation boss 214 can be the same or different. One first anti-off boss 213 and one anti-rotation boss 214 may each be distributed on a circumference, or a plurality of first anti-off bosses and a plurality of anti-rotation bosses may be uniformly or non-uniformly distributed on a circumference, respectively. For example, two first anti-off bosses 213 and two anti-rotation bosses 214 may be provided. The two first anti-off bosses 213 are symmetrically distributed on the circumference, while the two anti-rotation bosses 214 are symmetrically distributed on the circumference. This has the advantage that the front and the back do not need to be distinguished during mounting, which facilitates the mounting.

Figure 4:
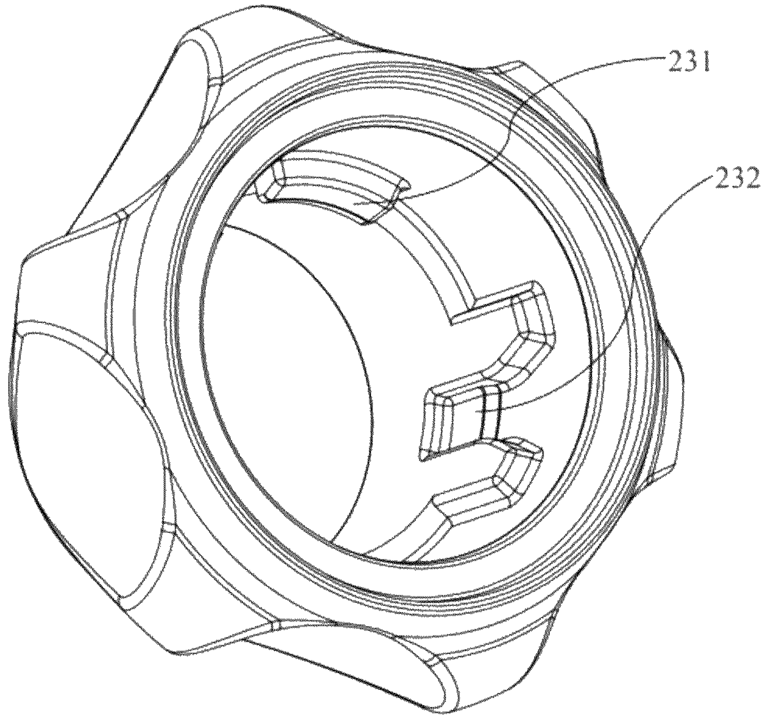
FIG. 4 is a schematically structural diagram of a thumb wheel outer ring of the present disclosure.

Correspondingly, as shown in FIG. 4, the thumb wheel outer ring 23 is provided with a second anti-off boss 231 and an anti-rotation groove 232. A quantity of the second anti-off boss 231 and a quantity of the anti-rotation groove 232 can be the same or different. One second anti-off boss 231 and one anti-rotation groove 232 may each be distributed on a circumference, or a plurality of second anti-off bosses and a plurality of anti-rotation grooves may be uniformly or non-uniformly distributed on a circumference, respectively. For example, two second anti-off bosses 231 and two anti-rotation grooves 232 may be provided. The two second anti-off bosses 231 are symmetrically distributed on the circumference, while the two anti-rotation grooves 232 are symmetrically distributed on the circumference. This has the advantage that the front and the back do not need to be distinguished during mounting, which facilitates the mounting.

To mount the thumb wheel outer ring 23 and the outer cannula assembly 21, the anti-rotation boss 214 and the first anti-off boss 213 on the outer cannula assembly 21 respectively enter the anti-rotation groove 232 and the second anti-off boss 231 of the thumb wheel outer ring. Due to a mutual clamping effect of the first anti-off boss 213 and the second anti-off boss 231, relative positions of the thumb wheel outer ring 23 and the outer cannula assembly 21 are fixed, so that the thumb wheel outer ring 23 cannot be separated from the outer cannula assembly 21 at the distal end. The anti-rotation boss 214 cooperates with the anti-rotation groove 232 to restrain relative rotation between the thumb wheel outer ring 23 and the outer cannula assembly 21.

Advantageously, to mount the thumb wheel outer ring 23 and the outer cannula assembly 21, the anti-rotation boss 214 on the outer cannula assembly 21 first enters the anti-rotation groove 232 of the thumb wheel outer ring 23 to determine an assembling position, and then the first anti-off boss 213 on the outer cannula assembly 21 cooperates with the second anti-off boss 231 of the thumb wheel outer ring 23. Due to the mutual clamping effect of the first anti-off boss 213 and the second anti-off boss 231, relative positions of the thumb wheel outer ring 23 and the outer cannula assembly 21 are fixed.

Advantageously, the anti-rotation boss 214 and the anti-rotation groove 232 are in interference fit or fixed by glue.

Advantageously, the cannula assembly 2 and the handle assembly 4 are provided with coaxial rotation connecting structures 215 that restrain axial movement, and the coaxial rotation connecting structures 215 can be coaxially connected to a handle on the outer cannula matrix 212. The coaxial rotation connecting structures 215 can also be coaxially connected to the handle on the thumb wheel outer ring 23.

Advantageously, the coaxial rotation connecting structure 215 is arranged on the outer cannula assembly 21, and the connecting structure 215 is connected to the handle assembly 4.

Figure 6:
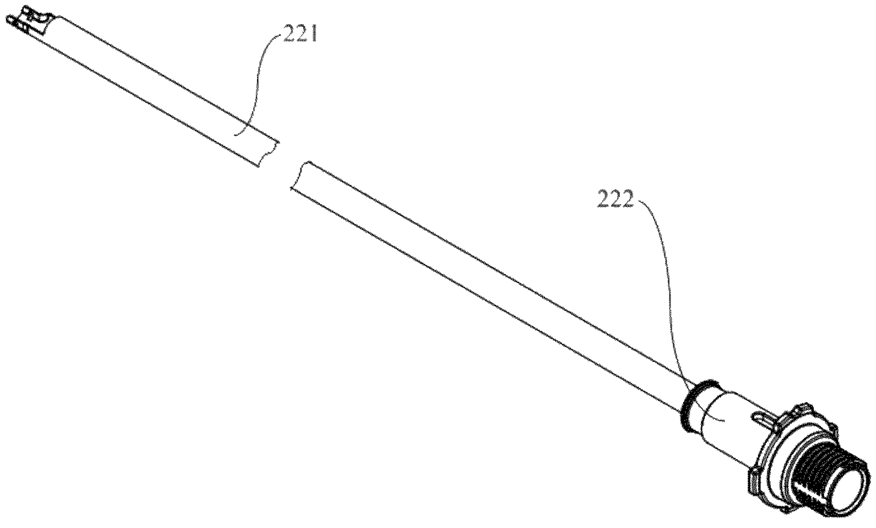
FIG. 6 is a schematic diagram of an inner cannula assembly of the present disclosure.

In an embodiment, as shown in FIG. 6, the inner cannula assembly 22 is composed of an inner cannula body 221 and an inner cannula matrix 222. The inner cannula body 221 and the inner cannula matrix 222 are assembled into a monolithic structure.

An optional process is to integrate the inner cannula body 221 and the inner cannula matrix 222 by a coinjection technology. The monolithic structure formed by the coinjection technology has no connection gap, and has high integrity and convenient use.

A further optional process is to integrate the inner cannula body 221 and the inner cannula matrix 222 by welding or gluing. The inner cannula assembly 22 formed by these fixed connection methods also has the advantages of high integrity and convenient use.

In an embodiment, a sealing structure is arranged between the matrix 231 of the outer cannula assembly 23 and the matrix 221 of the inner cannula assembly 22 to prevent tiny tissues or blood resulted from an operation from entering the handle assembly and contaminating the handle assembly, which causes the ultrasonic surgical instrument to be not reusable.

Figure 8:
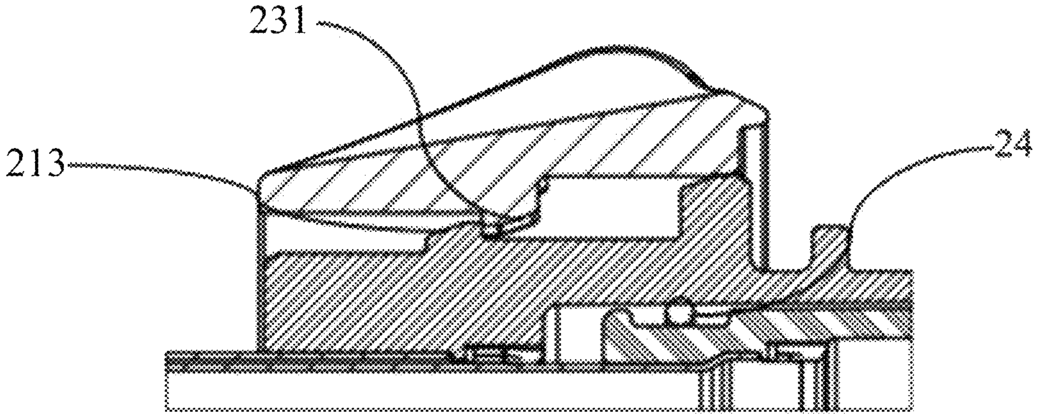
FIG. 8 is an enlarged diagram of the part A in FIG. 7.

Specifically, referring to FIG. 2 and FIG. 8, a sealing ring 24 can be arranged between the outer cannula matrix 212 of the outer cannula assembly 23 and the inner cannula matrix 222 of the inner tube assembly 22. The sealing ring 24 can seal a gap between the outer cannula matrix 212 and the inner cannula matrix 222, so as to prevent tiny tissues or blood from entering a lumen by the capillary action and prevent the handle assembly 4 from being contaminated.

Figure 7:
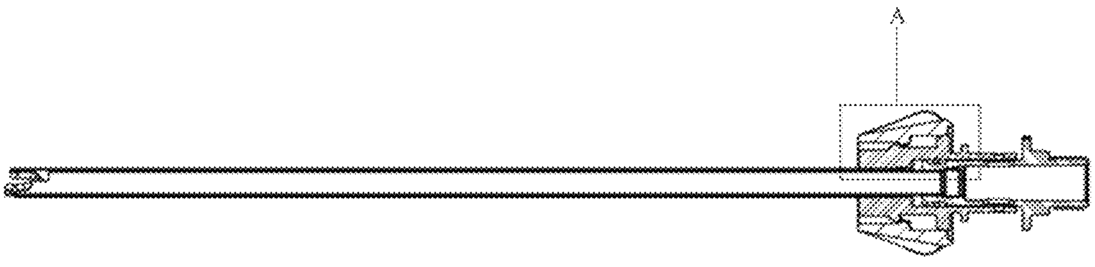
FIG. 7 is a schematic diagram of in-place mounting of a cannula assembly of the present disclosure.

FIG. 7 is a schematic diagram of completion of the mounting of the ultrasonic surgical instrument of the present disclosure. The inner cannula assembly 22 is coaxially assembled with the outer cannula assembly 21, and the thumb wheel outer ring 23 is coaxially mounted around the outer cannula assembly 21. A specific mounting process includes:

- step A: assembling the outer cannula body 211 and the outer cannula matrix 212 into the outer cannula assembly 21 by a coinjection molding process, a welding process, or a gluing process;
- step B: assembling the inner cannula body 221 and the inner cannula matrix 222 into the inner cannula assembly 22 by a coinjection molding process, a welding process, or a gluing process;
- step C: coaxially mounting the outer cannula assembly 21 and the inner cannula assembly 22 to obtain the cannula assembly 2; and
- step D: assembling the cannula assembly 2, the cutter bar 1, the jaw 3, and the handle assembly 4 to obtain the ultrasonic surgical instrument.

It should be noted that the sequence of step A and step B above can be reversed, that is, step B can be performed before step A.

Further, step A includes: assembling the outer cannula body 211 and the outer cannula matrix 212 into an integrated outer cannula assembly 21 by the coinjection molding process.

Step B includes: assembling the inner cannula body 221 and the inner cannula matrix 222 into an integrated inner cannula assembly 22 by the coinjection molding process.

Further, step C includes: coaxially mounting the sealing ring 24 onto the inner cannula assembly 22, and coaxially mounting the outer cannula assembly 21 onto the inner cannula assembly 22. That is, the sealing ring 24 is mounted between the outer cannula matrix 212 and the inner cannula matrix 222.

Further, the ultrasonic surgical instrument includes a thumb wheel outer ring 23. Step D includes: assembling the cannula assembly 2, the cutter bar 1, the jaw 3, the handle assembly 4, and the thumb wheel outer ring 23 to obtain the ultrasonic surgical instrument.

Further, the thumb wheel outer ring 23 and the outer cannula assembly 21 cannot rotate relative to each other.

Further, the cutter bar 1 is an ultrasonic cutter bar configured for transmitting ultrasonic energy. The cannula assembly 2 is coaxially mounted around the cutter bar 1. The jaw 3 is arranged at a distal end part of the cannula assembly 2, and the handle assembly 4 is arranged at a proximal end part of the cannula assembly 2.

Further, the outer cannula assembly 21 is provided with a first anti-off boss 213 and an anti-rotation boss 214, and the thumb wheel outer ring 23 is provided with a second anti-off boss 231 and an anti-rotation groove 232.

Further, to mount the thumb wheel outer ring 23 and the outer cannula assembly 21, the anti-rotation boss 214 and the first anti-off boss 213 on the outer cannula assembly 21 respectively enter the anti-rotation groove 232 and the second anti-off boss 231 of the thumb wheel outer ring 23, so that the thumb wheel outer ring 23 cannot be separated from the outer cannula assembly 21 towards the distal end.

During use of the ultrasonic surgical instrument of the present disclosure, the drive assembly in the handle assembly 4 actuates the inner cannula assembly 22, thereby opening or closing the jaw 3, so that the jaw 3 and the most distal end of cutter bar 1 achieve an opened state or a closed state.

During use, the circumferential rotation of the thumb wheel outer ring 23 actuate s the cannula assembly 2, the cutter bar 1, and the tongs 3 to rotate.

The ultrasonic surgical instrument according to the embodiments of the present disclosure may have the following beneficial effects:

1. The cannula assemblies are formed by the coinjection technology, the welding process, or the gluing process, and are further processed and assembled into the ultrasonic surgical instrument, so that the assembling procedures can be reduced.
2. The components formed by coinjection, welding, or gluing are high in integrity. The sealing between the inner and outer cannulas does not need to be achieved by designing complex configuration structures of cannulas. Expanded structures of the cannula parts can be eliminated or simplified. The overall structure is greatly simplified, and the performance is better optimized.
3. The ultrasonic surgical instrument of the present disclosure adopts the integrated cannula assemblies, which reduces the manufacturing costs.
4. The ultrasonic surgical instrument has a simple structure, and is convenient for assembling, easy to disassemble, clean, and disinfect.
5. A sealing structure is arranged between the inner cannula assembly and the outer cannula assembly, which can prevent tiny tissues or blood resulted from an operation from entering the handle assembly and causing contamination.
6. The ultrasonic surgical instrument of the present disclosure can be used in more precise surgical scenarios.

Figure 9:
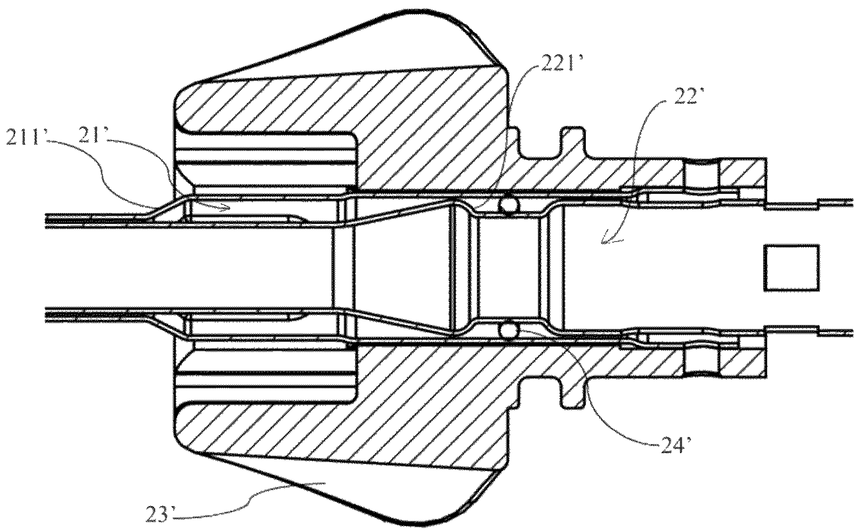
FIG. 9 is a schematic diagram of the prior art.

FIG. 9 is a schematic diagram of assembling in the prior art, which shows that a complex expanded structure needs to be designed between the inner cannula part and the outer cannula part, resulting in complex structure and poor performance.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

It should be noted that the implementation schemes in the accompanying drawings are only representative embodiments of the present disclosure, which is conducive to easy understanding by those skilled in the art. The protection scope of the present disclosure is not only limited to the scope limited by the implementation in the accompanying drawings, but also includes combination, variant, and modification of the implementation in the accompanying drawings.

It should be noted that terms "include", "including" or any other variants thereof herein are meant to cover non-exclusive inclusions, so that a process, method, object or device that includes a series of elements not only includes those elements, but also includes other elements which are not definitely listed, or further includes inherent elements of this process, method, object or device. Without more restrictions, elements defined by a sentence "includes a/an . . . " do not exclude that the process, method, object or device that includes the elements still includes other identical elements.

It should be finally noted that: the above embodiments are only used to describe the technical solutions of the present disclosure, and not intended to limit the present disclosure. Although the present disclosure has been described in detail with reference to the foregoing embodiments, those ordinarily skilled in the art should understand that they can still modify the technical solutions described in all the foregoing embodiments, or equivalently replace some of the technical features, and these modifications or replacements do not depart the essences of the corresponding technical solutions from the spirit and scope of the technical solutions of all the embodiments of the present disclosure.

What is claimed is:

1. An ultrasonic surgical instrument, comprising a cutter bar, a jaw, a cannula assembly, and a handle assembly, wherein the cutter bar is an ultrasonic cutter bar configured to transmit ultrasonic energy; the cannula assembly coaxially aligns with the cutter bar and is rotatably connected to the handle assembly; the jaw is arranged at a distal end part of the cannula assembly; the handle assembly is arranged at a proximal end part of the cannula assembly;

the cannula assembly comprises an inner cannula assembly, an outer cannula assembly sleeved onto the inner cannula assembly, and a thumb wheel outer ring coaxially mounted around the outer cannula assembly, wherein the outer cannula assembly comprises an outer cannula body and an outer cannula base formed into a monolithic structure and the inner cannula assembly comprises an inner cannula body and an inner cannula base formed into a monolithic structure and wherein the outer cannula assembly is axially provided with at least one first anti-off boss, the thumb wheel outer ring is provided with a second anti-off boss, and the at least one first anti-off boss abuts against the second anti-off boss to prevent the thumb wheel outer ring from separating from the outer cannula assembly towards a distal end of the cannula assembly.

2. The ultrasonic surgical instrument according to claim 1, wherein the rotatable connection between the outer cannula assembly and the handle assembly is unremovable, which restrains axial movement between the outer cannula assembly and the handle assembly.

3. The ultrasonic surgical instrument according to claim 1, wherein a connecting structure, rotating coaxially with the handle assembly, is arranged on the outer cannula assembly or the thumb wheel outer ring.

4. The ultrasonic surgical instrument according to claim 1, wherein the outer cannula assembly is axially provided with an anti-rotation boss radially extending from the outer cannula assembly, the thumb wheel outer ring is provided with an anti-rotation groove, and the anti-rotation boss cooperates with the anti-rotation groove; or the outer cannula assembly is axially provided with an anti-rotation groove, the thumb wheel outer ring is provided with an anti-rotation boss, and the anti-rotation boss cooperates with the anti-rotation groove.

5. The ultrasonic surgical instrument according to claim 1, wherein there are two first anti-off bosses; and the two first anti-off bosses are symmetrically distributed on a circumference.

6. The ultrasonic surgical instrument according to claim 1, wherein the thumb wheel outer ring and the outer cannula assembly are assembled by interference fit or gluing, so that the thumb wheel outer ring and the outer cannula assembly do not rotate relative to each other.

7. The ultrasonic surgical instrument according to claim 1, wherein the jaw and a distal end of the cutter bar form a clamping structure; the outer cannula assembly and the inner cannula assembly are coaxially assembled; the inner cannula assembly is located between the cutter bar and the outer cannula assembly; and a drive assembly of the handle assembly actuates the inner cannula assembly to open or close the jaw, so that the jaw and the distal end of the cutter bar achieve an opened state or a closed state.

8. The ultrasonic surgical instrument according to claim 1, wherein the ultrasonic surgical instrument comprises a sealing ring; the sealing ring is located between the outer cannula assembly and the inner cannula assembly; and the sealing ring is located between the outer cannula base of the outer cannula assembly and the inner cannula base of the inner cannula assembly.

* * * * *